US012568195B2

(12) United States Patent
Lee et al.

(10) Patent No.: US 12,568,195 B2
(45) Date of Patent: Mar. 3, 2026

(54) STEREOSCOPIC SCANNING METHOD, STEREOSCOPIC IMAGE ANALYSIS METHOD AND SCANNING APPARATUS

(71) Applicant: QISDA CORPORATION, Taoyuan City (TW)

(72) Inventors: Tsung-Hsi Lee, Taoyuan City (TW); Chuang-Wei Wu, Taoyuan City (TW)

(73) Assignee: Qisda Corporation, Taoyuan City (TW)

( * ) Notice: Subject to any disclaimer, the term of this patent is extended or adjusted under 35 U.S.C. 154(b) by 0 days.

(21) Appl. No.: 19/015,677

(22) Filed: Jan. 10, 2025

(65) Prior Publication Data

US 2025/0310501 A1     Oct. 2, 2025

(30) Foreign Application Priority Data

Mar. 28, 2024     (CN) ......................... 202410363699.1

(51) Int. Cl.
| | |
|---|---|
| *H04N 13/161* | (2018.01) |
| *A61B 1/00* | (2006.01) |
| *A61B 1/24* | (2006.01) |
| *G06T 7/00* | (2017.01) |
| *G06T 7/521* | (2017.01) |
| *G06T 7/593* | (2017.01) |
| *H04N 13/156* | (2018.01) |
| *H04N 13/194* | (2018.01) |
| *H04N 13/254* | (2018.01) |

(52) U.S. Cl.
CPC ....... *H04N 13/161* (2018.05); *A61B 1/00172* (2013.01); *A61B 1/24* (2013.01); *G06T 7/0014* (2013.01); *G06T 7/521* (2017.01); *G06T 7/593*

(2017.01); *H04N 13/156* (2018.05); *H04N 13/194* (2018.05); *H04N 13/254* (2018.05); *G06T 2207/10012* (2013.01); *G06T 2207/30036* (2013.01)

(58) Field of Classification Search
None
See application file for complete search history.

(56) References Cited

U.S. PATENT DOCUMENTS

| | | | | |
|---|---|---|---|---|
| 6,111,605 A | * | 8/2000 | Suzuki ................. | H04N 1/3871 |
| | | | | 348/220.1 |
| 11,367,192 B2 | * | 6/2022 | Kopelman ............. | G16H 50/50 |

(Continued)

FOREIGN PATENT DOCUMENTS

| | | |
|---|---|---|
| EP | 3662839 | 10/2020 |
| KR | 101792542 | 3/2016 |
| KR | 101872165 | 6/2018 |

*Primary Examiner* — Clifford Hilaire

(57) ABSTRACT

A stereoscopic scanning method is applied to a scanning apparatus having a structured light generator and an optical sensor and applied for a stereoscopic image analysis method. The stereoscopic scanning method includes utilizing the structured light generator to project a structured light pattern onto a target object, controlling the optical sensor to capture the target object for acquiring a detection image, analyzing and determining whether the structured light pattern is existed on the target object inside the detection image, and applying a first compression mode or a second compression mode to the detection image in accordance with a determined result of the structured light pattern.

19 Claims, 7 Drawing Sheets

(56)  References Cited

U.S. PATENT DOCUMENTS

| | | | |
|---|---|---|---|
| 2012/0148986 A1* | 6/2012 | Yan | G06T 5/70 |
| | | | 433/215 |
| 2013/0129245 A1* | 5/2013 | Tin | H04N 19/60 |
| | | | 382/248 |
| 2014/0267173 A1* | 9/2014 | Liu | G06F 3/0421 |
| | | | 345/175 |
| 2018/0144535 A1* | 5/2018 | Ford | G06T 15/005 |
| 2020/0242831 A1* | 7/2020 | LaMontagne | G06T 19/00 |
| 2021/0389654 A1* | 12/2021 | Lee | G02B 13/16 |
| 2024/0023800 A1* | 1/2024 | Fridman | A61B 1/00052 |
| 2025/0088753 A1* | 3/2025 | Ouellet | H04N 23/73 |

* cited by examiner

Id

Id

Id

Id

STEREOSCOPIC SCANNING METHOD, STEREOSCOPIC IMAGE ANALYSIS METHOD AND SCANNING APPARATUS

BACKGROUND OF THE INVENTION

1. Field of the Invention

The present invention relates to a stereoscopic scanning method and a stereoscopic image analysis method and a related scanning apparatus, and more particularly, to a stereoscopic scanning method and a stereoscopic image analysis method and a related scanning apparatus having preferred image compression efficiency.

2. Description of the Prior Art

A conventional oral scanner is electrically connected to an external computer in a wired manner or in a wireless manner; computation power of the oral scanner is lower than computation power of the external computer, so the oral scanner captures two-dimensional images inside the oral cavity and then transmits the two-dimensional images to the external computer for creating a three-dimensional model of the tooth. When the oral scanner takes the two-dimensional image of the oral cavity, the two-dimensional image may contain a large area of the gums due to placement of the oral scanner. The two-dimensional image that only contains the small area of the tooth is classified as invalid data, but the invalid data is still transmitted from the oral scanner to the external computer for analysis and judgment, which wastes transmission bandwidth. Although the conventional wireless oral scanner compresses the two-dimensional image before transmission due to transmission bandwidth limitation, the decompressed image restored from the two-dimensional image that contains the large area of the tooth and is greatly compressed does not have the acceptable image quality. Therefore, design of a stereoscopic scanning method and a stereoscopic image analysis method and a related scanning apparatus of identifying different two-dimensional images of the oral scanner respectively suitable for the high image compression rate or the low image compression rate so as to maintain the image quality of the effective data and reduce the bandwidth requirement of the invalid data is an important issue in the related medical apparatus industry.

SUMMARY OF THE INVENTION

The present invention provides a stereoscopic scanning method and a stereoscopic image analysis method and a related scanning apparatus having preferred image compression efficiency for solving above drawbacks.

According to the claimed invention, a stereoscopic scanning method is applied to a stereoscopic scanning device having a structured light generator and an optical sensor. The stereoscopic scanning method includes driving the structured light generator to project a structured light pattern onto a target object, driving the optical sensor to capture a detection image of the target object, analyzing detection image to determine whether the structured light pattern is existed on the target object contained by the detection image, and applying a first compression mode or a second compression mode for the detection image in accordance with a determined result of the structured light pattern.

According to the claimed invention, a stereoscopic image analysis method is applied to a stereoscopic image analysis device electrically connected with a stereoscopic scanning device. The stereoscopic image analysis method includes executing a decompression process on a received image to acquire a decompressed image, utilizing a deep learning model to acquire pixel feature information of a target object in the decompressed image, comparing the pixel feature information with a preset range threshold, and outputting a control command to the stereoscopic scanning device for adjusting its image compression rate in accordance with a comparison result of the pixel feature information and the preset range threshold. The pixel feature information is a ratio of a number of pixels contained by the target object to a number of all pixels of the decompressed image.

According to the claimed invention, a scanning apparatus of scanning a target object includes a stereoscopic scanning device and a stereoscopic image analysis device. The stereoscopic scanning device includes a structured light generator, an optical sensor, a first transceiver module and an operation processor. The structured light generator is adapted to project a structured light pattern onto the target object. The optical sensor is adapted to capture a detection image of the target object. The operation processor is electrically connected with the structured light generator and the optical sensor and the first transceiver module. The operation processor is adapted to analyze the detection image for determining whether the structured light pattern is existed on the target object contained by the detection image, decide to apply a first compression mode or a second compression mode for the detection image in accordance with a determined result of the structured light pattern, and utilize the first transceiver module to transmit the compressed detection image. The stereoscopic image analysis device is electrically connected with the stereoscopic scanning device. The stereoscopic image analysis device includes a second transceiver module and an operation module. The second transceiver module is adapted to receive the compressed detection image. The operation module is electrically connected with the second transceiver module. The operation module is adapted to execute a decompression process on the compressed detection image for acquiring a decompressed image, utilize a deep learning model to acquire pixel feature information of a target object in the decompressed image, compare the pixel feature information with a preset range threshold, and output a control command to the stereoscopic scanning device in accordance with a comparison result of the pixel feature information and the preset range threshold.

The scanning apparatus of the present invention can include the stereoscopic scanning device and the stereoscopic image analysis device; computation power of the stereoscopic scanning device can be lower than computation power of the stereoscopic image analysis device, and the stereoscopic scanning device can execute the stereoscopic scanning method of the present invention to determine whether different detection images are suitable for different image compression rates, or whether different regions of the detection image are suitable for different image compression rates. Thus, the detection image or the related regions that contains the large area of the target object can be processed by the low image compression rate to maintain the image quality, and the detection image or the related regions that contains the small area of the target object or does not contain the target object can be processed by the high image compression rate to economize computation and transmission performance. The stereoscopic image analysis device can execute the stereoscopic image analysis method of the present invention to determine the coverage of the decompressed image for the target object, so as to decide the following image compression rate and notify the stereoscopic scanning device.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
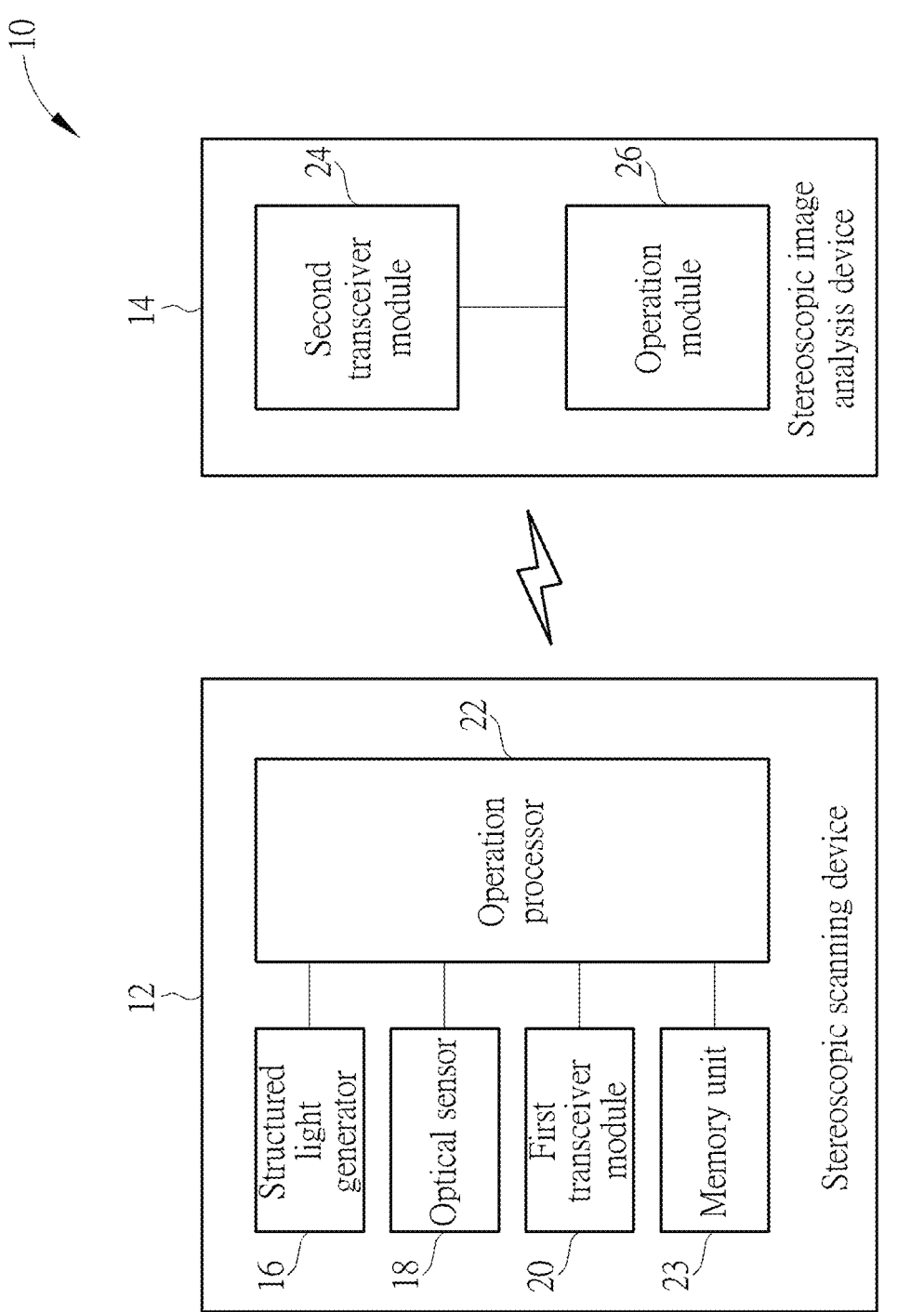
FIG. 1 is a functional block diagram of a scanning apparatus according to an embodiment of the present invention.
Figure 2:
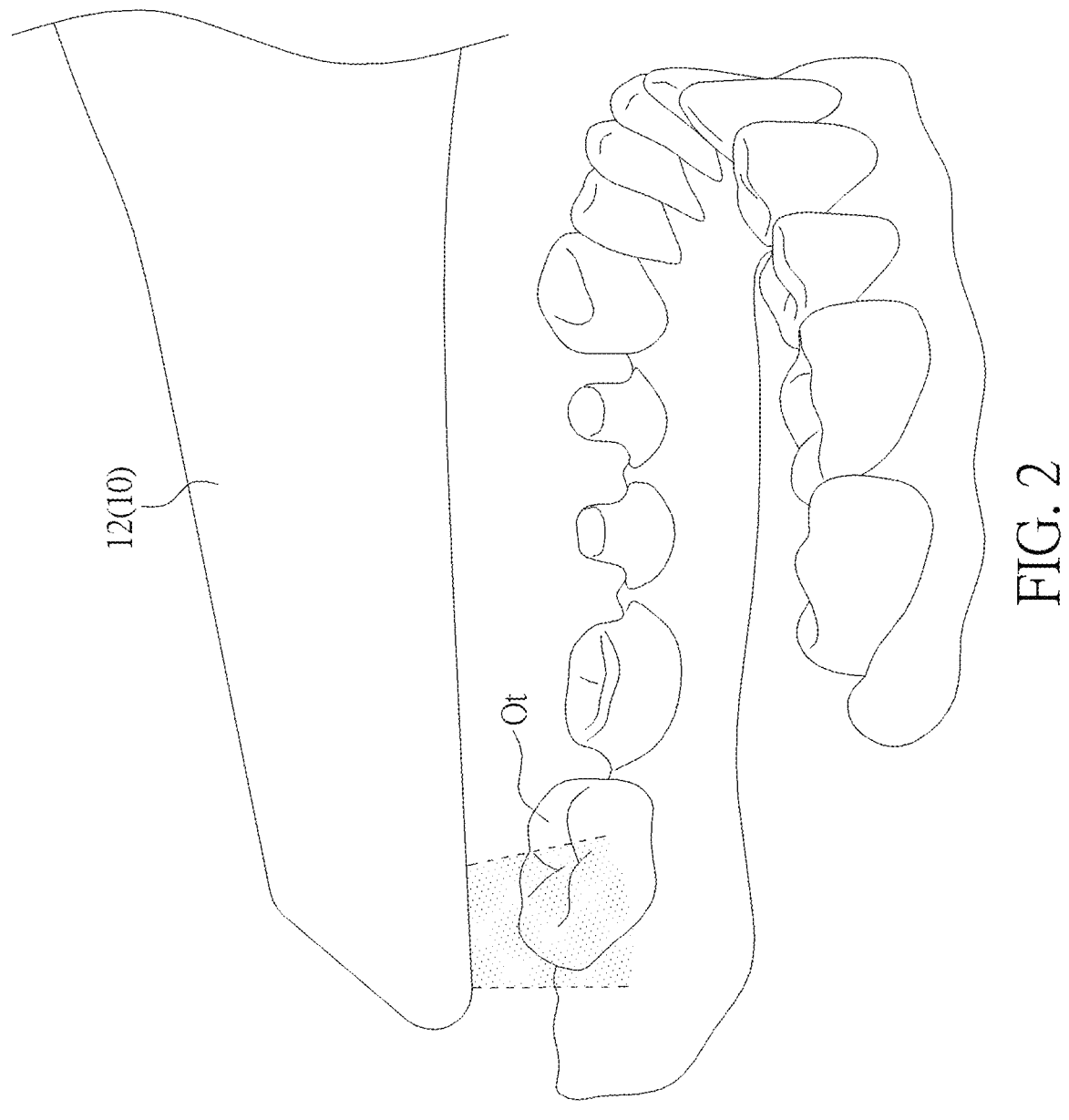
FIG. 2 is an application diagram of the scanning apparatus according to the embodiment of the present invention.

Please refer to FIG. 1 and FIG. 2. FIG. 1 is a functional block diagram of a scanning apparatus 10 according to an embodiment of the present invention. FIG. 2 is an application diagram of the scanning apparatus 10 according to the embodiment of the present invention. The scanning apparatus 10 can be an oral scanning apparatus used to scan, model and stitch images of a target object Ot (such as a tooth). The scanning apparatus 10 can include a stereoscopic scanning device 12 and a stereoscopic image analysis device 14 electrically connected with in a wired manner or in a wireless manner. The stereoscopic scanning device 12 can be an intraoral scanner, and used to capture a 2D image, or capture and transform one-dimensional images into the 2D image, and transmit the 2D image to the stereoscopic image analysis device 14 for following process. The stereoscopic image analysis device 14 can be an operation device with both two-dimensional and three-dimensional image computing functions, such as a personal computer, a notebook computer or a tablet computer. The stereoscopic image analysis device 14 can be communicated with the stereoscopic scanning device 12, and acquire and analyze the 2D image transmitted from the stereoscopic scanning device 12 to generate a three-dimensional model of the target object Ot, as shown in FIG. 2.

The stereoscopic scanning device 12 can include a structured light generator 16, an optical sensor 18, a first transceiver module 20 and an operation processor 22 electrically connected with each other. The structured light generator 16 can be a common stripe pattern generator used to project a structured light pattern onto the target object Ot. The optical sensor 18 can capture the two-dimensional detection image of the target object Ot. The operation processor 22 can analyze the detection image and determine whether the structured light pattern is existed on the target object Ot contained by the detection image, and decide to apply a first compression mode or a second compression mode for the detection image in accordance with a determined result of the structured light pattern; then, the compressed detection image can be transmitted to the stereoscopic image analysis device 14 via the first transceiver module.

The stereoscopic image analysis device 14 can include a second transceiver module 24 and an operation module 26 electrically connected with each other. The second transceiver module 24 can receive the compressed detection image transmitted by the first transceiver module 20 of the stereoscopic scanning device 12 in the wired manner or in the wireless manner. The operation module 26 can execute a decompression process on the compressed detection image to acquire a decompressed image, and utilize a deep learning model relevant to the dental image to acquire pixel feature information of the target object Ot in the decompressed image; the pixel feature information of the target object Ot can be interpreted as a range of the target object Ot within an image frame. The operation module 26 can output a control command to the stereoscopic scanning device 12 in accordance with the pixel feature information of the target object Ot. For example, the control command can drive the stereoscopic scanning device 12 to capture a next detection image, or can provide a compression parameter relevant to the image compression rate towards the stereoscopic scanning device 12; practical application of the control command can depend on an actual demand.

Figure 3:
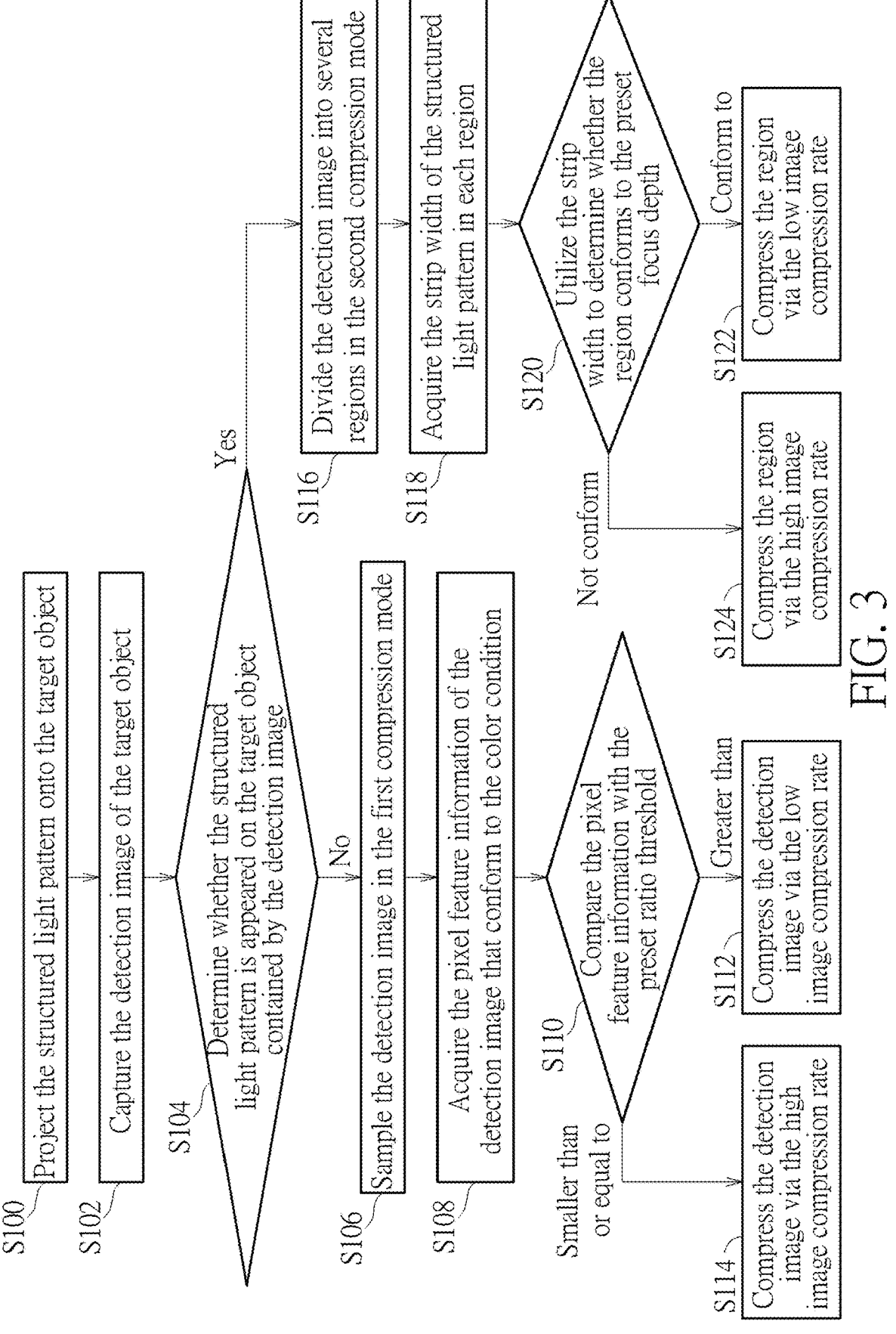
FIG. 3 is a flow chart of a stereoscopic scanning method according to the embodiment of the present invention.
Figure 4:
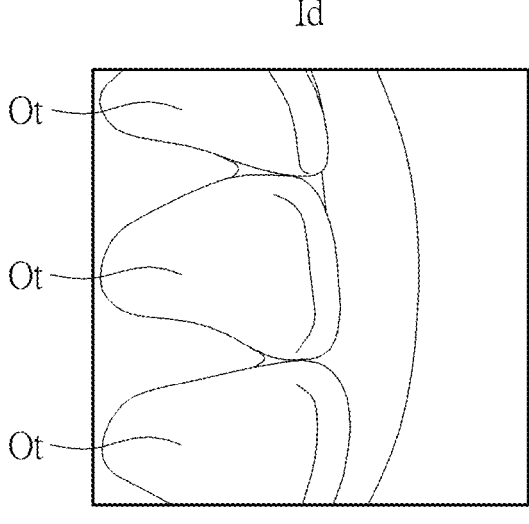
FIG. 4 to FIG. 6 are diagrams of a detection image in different stages according to the embodiment of the present invention.
Figure 5:
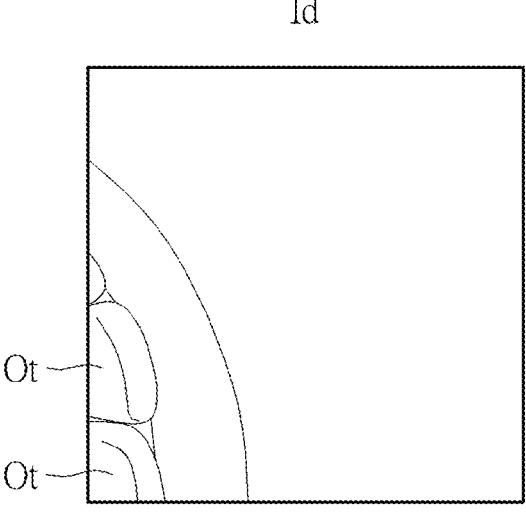
Figure 6:
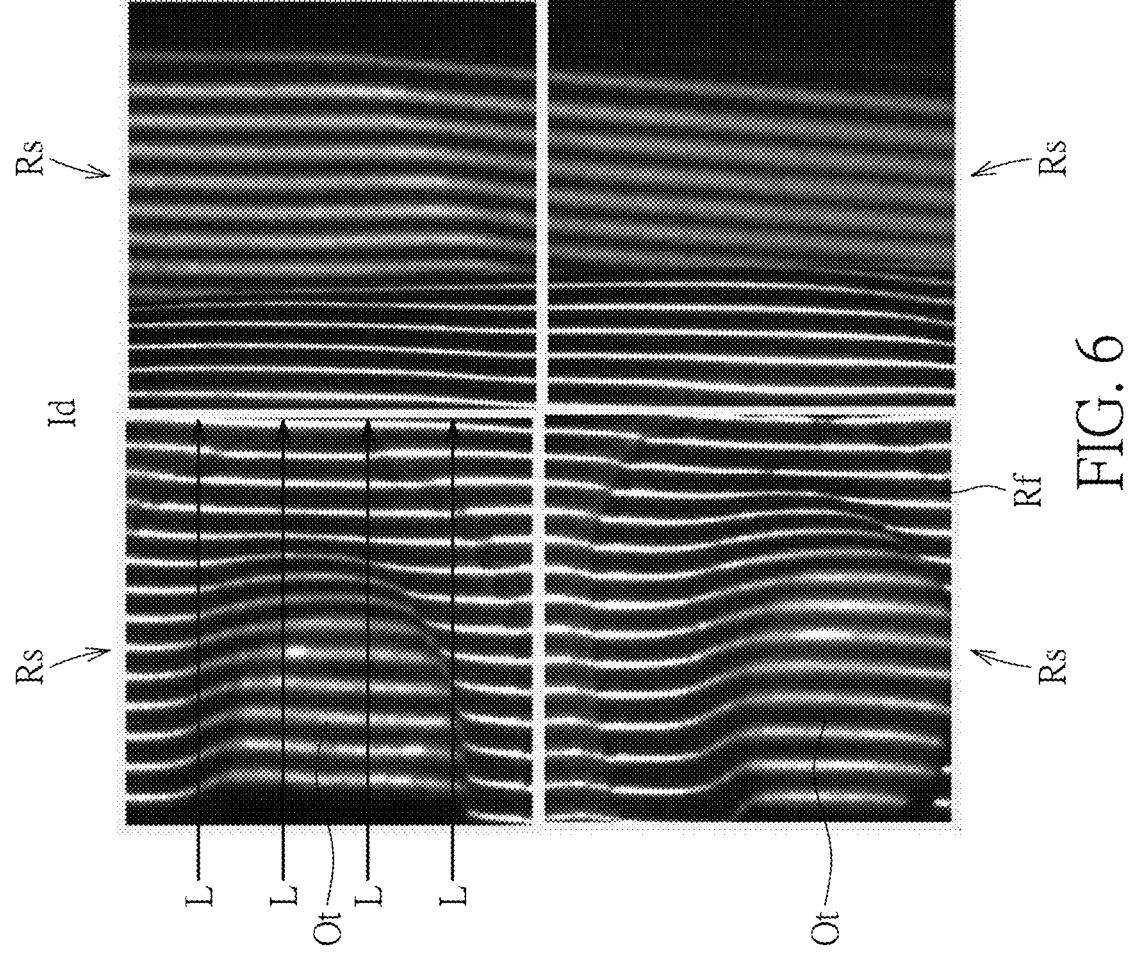

Please refer to FIG. 3 to FIG. 6. FIG. 3 is a flow chart of a stereoscopic scanning method according to the embodiment of the present invention. The stereoscopic scanning method can be applied for the stereoscopic scanning device 12. FIG. 4 to FIG. 6 are diagrams of the detection image Id in different stages according to the embodiment of the present invention. First, step S100, step S102 and step S104 can be executed that the operation processor 22 can control the structured light generator 16 to project the structured light pattern onto the target object Ot, and control the optical sensor 18 to capture the detection image Id of the target object Ot, and analyze the detection image Id to determine whether the structured light pattern is existed or appeared on the target object Ot contained by the detection image Id. If the structured light pattern is not existed on the target object Ot contained by the detection image Id, step S106 can be executed to sample a plurality of pixels of the detection image Id in the first compression mode. In step S106, all pixels of the detection image Id can be sampled; or partial pixels spaced from each other in a preset distance of the detection image Id can be sampled, such as sampling every eight or sixteen pixels to achieve an aim of the downsampling result.

Then, step S108 and step S110 can be executed to acquire the pixel feature information of the plurality of pixels that conform to a color condition, and compare the pixel feature information with a preset ratio threshold. As mentioned above, the target object Ot can be the tooth, and the color condition can be the main color of the tooth, such as yellow or white; actual application of the color condition is not limited to the foresaid embodiment. The pixel feature information can be interpreted as a ratio of a number of pixels among the plurality of pixels that conforms to the color condition to a number of pixels among the plurality of pixels that does not conform to the color condition. The preset ratio threshold can depend on the design demand, such as twenty percent, forth percent or sixty percent; an actual value of the preset ratio threshold can be varied in accordance with the design demand. In other possible embodiment, the preset ratio threshold may be defined as the pixel feature information of a previous detection image Id captured by the optical sensor 18 that conforms to the color condition.

If the pixel feature information is greater than the preset ratio threshold, the detection image Id may contain the large area of the target object Ot, as shown in FIG. 4, and step S112 can be executed to compress the detection image Id via a low image compression rate for transmission. If the pixel feature information is smaller than or equal to the preset ratio threshold, the detection image Id may contain a large number of objects that do not belong to the target object Ot, such as soft tissue (the gums, the tongue, the lips, or the cheek muscles) shown in FIG. 5, and step S114 can be executed to compress the detection image Id via a high image compression rate for transmission. Therefore, the stereoscopic scanning method of the present invention can utilize a comparison result of the ratio of the number of pixels in the detection image Id that conforms to the color condition to the number of pixels in the detection image Id that does not conform to the color condition and the preset ratio threshold, to decide the image compression rate of the detection image Id when the structured light pattern is not existed on the target object Ot contained by the detection image Id.

It should be mentioned that the optical sensor 18 can be a monochromatic light sensing module or a color light sensor. When the optical sensor 18 is the monochromatic light sensing module, the stereoscopic scanning device 12 can stitch monochromatic detection images Id respectively acquired by several monochromatic sensors of the monochromatic light sensing module to acquire the colorful detection image Id, and then apply the colorful detection image Id to the stereoscopic scanning method of the present invention for compression and transmission. When the optical sensor 18 is the color light sensor, the colorful detection image Id acquired by the color light sensor can be directly applied to the stereoscopic scanning method of the present invention for compression and transmission.

As shown in FIG. 6, if the structured light pattern Pf is existed on the target object Ot contained by the detection image Id, step S116 and step S118 can be executed to divide the detection image Id into several regions Rs in the second compression mode, such as the 2×2 regions, and acquire a strip width of the structured light pattern Pf in each region Rs. The strip width can be defined as an average width of all stripes or partial stripes of the structured light pattern Pf in each region Rs. If the strip width conforms to a preset width, the region Rs corresponding to the strip width can be located at a suitable depth of field range; if the strip width does not conform to the preset width, the region Rs corresponding to the strip width can be outside the suitable depth of field range.

Therefore, step S120 can be continuously executed to utilize the strip width to determine whether each region Rs conforms to a preset focus depth; the preset focus depth may be defined as the foresaid suitable depth of field range. If the region Rs that corresponds to the strip width conforms to the preset focus depth, the region R may contain the target object Ot (which means the tooth is photographed), as the left region Rs shown in FIG. 6, and step S122 can be executed to compress the region Rs via the low image compression rate for transmission. If the region Rs that corresponds to the strip width does not conform to the preset focus depth, the region Rs may not contain the target object Ot (which means the gums is photographed), as the right region Rs shown in FIG. 6, and step S124 can be executed to compress the region Rs via the high image compression rate for transmission.

In the present invention, the actual values of the suitable depth of field range and the preset focus depth can depend on parameters of hardware and software of the stereoscopic scanning device 12, and the detailed description is omitted herein for simplicity. In step S118, the stereoscopic scanning method of the present invention can set at least one sampling line L intersected with several stripes of the structured light pattern Pf in each region Rs; for example, there are four sampling lines L set at even intervals in an upper section and a lower section of the region Rs. Then, the stereoscopic scanning method can analyze a pixel intensity distribution curve of each sampling line L, and determine the strip width of each stripe in accordance with the pixel intensity distribution curve. The foresaid embodiment is one application of the present invention, and the actual application is not limited thereto, so other possible application is omitted herein for simplicity.

Step S124 can compress the region Rs of the detection image Id that has the structured light pattern Pf via the high image compression rate; in the meantime, the stereoscopic scanning method of the present invention can acquire line center information of all stripes of the structured light pattern Pf in the region Rs, and attach the line center information to a data packet of the compressed region Rs for transmitting towards the stereoscopic image analysis device 14. The line center information can be used to help the stereoscopic image analysis device 14 constructs three-dimensional depth information from the 2D image (which means the several regions Rs of the detection image Id) provided by the stereoscopic scanning device 12. When the stereoscopic image analysis device 14 acquires and analyzes the region Rs that is compressed by the high image compression rate does not conform to a stitching condition, an image quality of the region Rs that is compressed by the high image compression rate is worse after restoration, which affects an accuracy of the 3D model, and the stereoscopic image analysis device 14 can output the related switching command. When the stereoscopic scanning device 12 receives the switching command relevant to an image stitching result of the compressed region Rs and the line center information from the stereoscopic image analysis device 14, the stereoscopic scanning device 12 can decide whether to decrease the high image compression rate used in step S124 in accordance with the switching command; the decreased high image compression rate can be preferably greater than the low image compression rate used in step S122.

Besides, the stereoscopic scanning device 12 can further include a memory unit 23 electrically connected with the operation processor 22. The memory unit 23 can store parameters of the preset ratio threshold and the image compression rate applied for the first compression mode, and the preset focus depth and the image compression rate applied for the second compression mode. The present invention does not limit actual compression parameters of the low image compression rate and the high image compression rate mentioned in step S112 and step S114, and step S122 and step S124. Any parameter of obviously improving image transmission performance to comply with the bandwidth limitation by compression results of the low image compression rate and the high image compression rate can conform to the design scope of the present invention.

Figure 7:
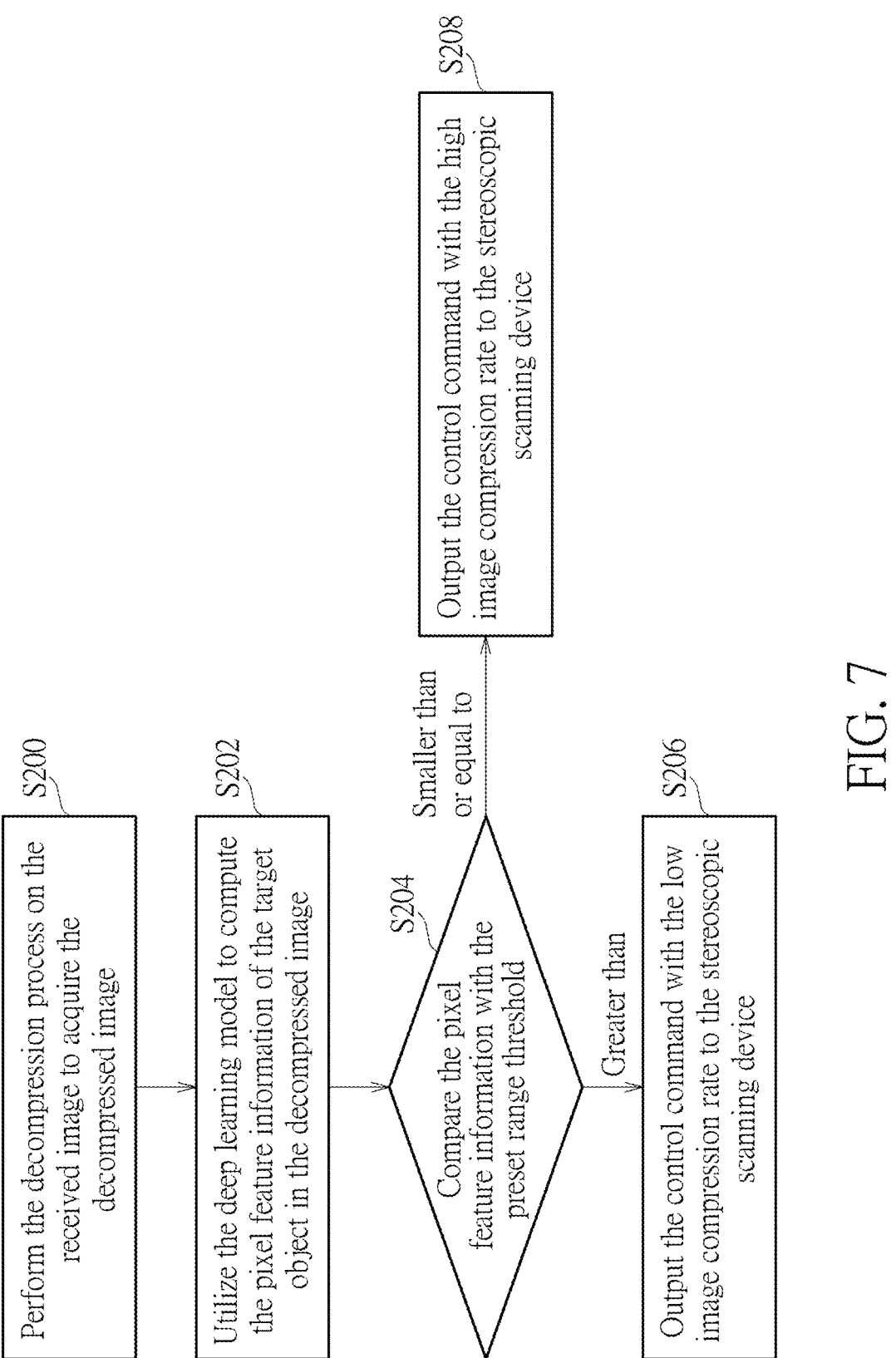
FIG. 7 is a flow chart of a stereoscopic image analysis method according to the embodiment of the present invention.
Figure 8:
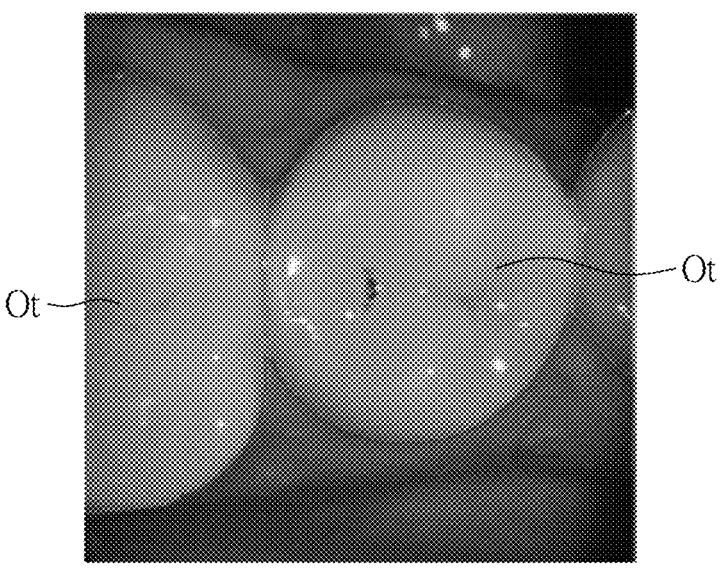
FIG. 8 and FIG. 9 are diagrams of a detection image in different stages according to the embodiment of the present invention.
Figure 9:
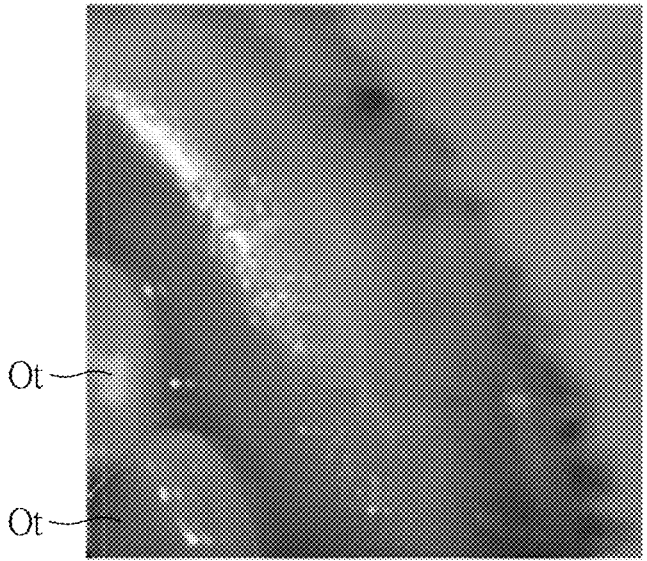

Please refer to FIG. 7 to FIG. 9. FIG. 7 is a flow chart of a stereoscopic image analysis method according to the embodiment of the present invention. FIG. 8 and FIG. 9 are diagrams of the detection image Id in different stages according to the embodiment of the present invention. The stereoscopic image analysis method can be applied for the stereoscopic image analysis device 14. First, step S200, step S202 and step S204 can be executed to acquire the received image from the stereoscopic scanning device 12 for performing the decompression process and acquiring the decompressed image, utilize the deep learning model to compute the pixel feature information of the target object Ot in the decompressed image, and compare the pixel feature information with the preset range threshold. The pixel feature information of the target object Ot can be defined as the ratio of the number of pixels contained by the target object Ot to the number of all pixels in the decompressed image. When the pixel feature information is greater than the preset range threshold, the decompressed image contains the large area of the target object Ot, as shown in FIG. 8, and step S206 can be executed to output the control command with the low image compression rate to the stereoscopic scanning device 12; when the pixel feature information is smaller than or equal to the preset range threshold, the decompressed image does not contain the large area of the target object Ot, as shown in FIG. 9, and step S208 can be executed to output the control command with the high image compression rate to the stereoscopic scanning device 12.

The deep learning model in step S202 can use a pre-training machine learning model to identify the target object Ot and other background (such as the gums) in the decompressed image. The establishment and training process of the machine learning model is not limited to any type; any model that can accurately identify the tooth and the gums in the image can belong to the design scope of the present invention, and the detailed description is omitted herein for simplicity. When the stereoscopic image analysis method outputs the control command with the high image compression rate to the stereoscopic scanning device 12, the stereoscopic scanning device 12 can send the decompressed image having the structured light pattern (such as the structured light pattern Pf of the detection image Id shown in FIG. 6) back to the stereoscopic image analysis device 14. The stereoscopic image analysis method of the present invention can acquire the related line center information when getting the received image (which means the compressed detection image Id or the related regions Rs transmitted by the stereoscopic scanning method), and utilize the line center information to decode the structured light pattern in the decompressed image for computing depth information. As mentioned above, if the decompressed image does not conform to the stitching condition, the stereoscopic image analysis method can decide whether to output the switching command to the stereoscopic scanning device 12 for decreasing the compression parameter of the control command with the high image compression rate in accordance with the image decoding result of the decompressed image.

In conclusion, the scanning apparatus of the present invention can include the stereoscopic scanning device and the stereoscopic image analysis device; computation power of the stereoscopic scanning device can be lower than computation power of the stereoscopic image analysis device, and the stereoscopic scanning device can execute the stereoscopic scanning method of the present invention to determine whether different detection images are suitable for different image compression rates, or whether different regions of the detection image are suitable for different image compression rates. Thus, the detection image or the related regions that contains the large area of the target object can be processed by the low image compression rate to maintain the image quality, and the detection image or the related regions that contains the small area of the target object or does not contain the target object can be processed by the high image compression rate to economize computation and transmission performance. The stereoscopic image analysis device can execute the stereoscopic image analysis method of the present invention to determine the coverage of the decompressed image for the target object, so as to decide the following image compression rate and notify the stereoscopic scanning device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A stereoscopic scanning method applied to a stereoscopic scanning device having a structured light generator and an optical sensor, the stereoscopic scanning method comprising:

driving the structured light generator to project a structured light pattern onto a target object;

driving the optical sensor to capture a detection image of the target object;

determining whether the structured light pattern is existed on the target object contained by the detection image according to analysis of the detection image;

executing a first compression mode to sample a plurality of pixels of the detection image when the structured light pattern is not existed on the target object contained by the detection image;

acquiring pixel feature information of the plurality of pixels that conforms to a color condition;

comparing the pixel feature information with a preset ratio threshold; and deciding an image compression rate of the detection image in accordance with a comparison result of the pixel feature information and the preset ratio threshold;

wherein the pixel feature information is a ratio of a number of pixels among the plurality of pixels that conforms to the color condition to a number of pixels among the plurality of pixels that does not conform to the color condition.

2. The stereoscopic scanning method of claim 1, wherein the plurality of pixels is all pixels of the detection image, or is partial pixels of the detection image that are spaced from each other in a preset distance.

3. The stereoscopic scanning method of claim 1, wherein the stereoscopic scanning method utilizes a low image compression rate to compress the detection image for transmission when the pixel feature information is greater than the preset ratio threshold; the stereoscopic scanning method utilizes a high image compression rate to compress the detection image for the transmission when the pixel feature information is smaller than or equal to the preset ratio threshold.

4. The stereoscopic scanning method of claim 1, wherein the preset ratio threshold is the pixel feature information of a previous detection image captured by the optical sensor that conforms to the color condition.

5. A stereoscopic image analysis method applied to a stereoscopic image analysis device electrically connected with a stereoscopic scanning device, the stereoscopic image analysis method comprising:

executing a decompression process on a received image to acquire a decompressed image;

utilizing a deep learning model to acquire pixel feature information of a target object in the decompressed image;

comparing the pixel feature information with a preset range threshold; and outputting a control command to the stereoscopic scanning device for adjusting its image compression rate in accordance with a comparison result of the pixel feature information and the preset range threshold;

wherein the pixel feature information is a ratio of a number of pixels contained by the target object to a number of all pixels of the decompressed image.

6. The stereoscopic image analysis method of claim 5, wherein the stereoscopic image analysis method outputs the control command with a low image compression rate when the pixel feature information is greater than the preset range threshold; the stereoscopic image analysis method outputs the control command with a high image compression rate when the pixel feature information is smaller than or equal to the preset range threshold.

7. The stereoscopic image analysis method of claim 6, wherein the decompressed image comprises a structured light pattern, the stereoscopic image analysis method further comprises:

receiving line center information of all strips of the structured light pattern transmitted from the stereoscopic scanning device when outputting the control command with the high image compression rate; and stitching the decompressed image by the line center information.

8. The stereoscopic image analysis method of claim 7, further comprising:

deciding whether to output a switching command to the stereoscopic scanning device for decreasing the high image compression rate of the control command in accordance with an image decoding result of the decompressed image.

9. A scanning apparatus of scanning a target object, comprising:

a stereoscopic scanning device, comprising:

a structured light generator adapted to project a structured light pattern onto the target object;

an optical sensor adapted to capture a detection image of the target object;

a first transceiver module; and an operation processor electrically connected with the structured light generator and the optical sensor and the first transceiver module, the operation processor being adapted to analyze the detection image for determining whether the structured light pattern is existed on the target object contained by the detection image, decide to apply a first compression mode or a second compression mode for the detection image in accordance with a determined result of the structured light pattern, and utilize the first transceiver module to transmit the compressed detection image; and a stereoscopic image analysis device electrically connected with the stereoscopic scanning device, the stereoscopic image analysis device comprising:

a second transceiver module adapted to receive the compressed detection image; and an operation module electrically connected with the second transceiver module, the operation module being adapted to execute a decompression process on the compressed detection image for acquiring a decompressed image, utilize a deep learning model to acquire pixel feature information of a target object in the decompressed image, compare the pixel feature information with a preset range threshold, and output a control command to the stereoscopic scanning device in accordance with a comparison result of the pixel feature information and the preset range threshold.

10. The scanning apparatus of claim 9, wherein the control command drives the stereoscopic scanning device to capture a next detection image, or the control command is a compression parameter relevant to an image compression rate.

11. The scanning apparatus of claim 9, wherein the operation processor is adapted to further execute the first compression mode to sample a plurality of pixels of the detection image when the structured light pattern is not existed on the target object contained by the detection image, acquire pixel feature information of the plurality of pixels that conforms to a color condition, compare the pixel feature information with a preset ratio threshold, and decide the detection image is compressed by a high image compression rate or a low image compression rate in accordance with a comparison result of the pixel feature information and the preset ratio threshold.

12. The scanning apparatus of claim 9, wherein the operation processor is adapted to further execute the second compression mode to divide the detection image into several regions when the structured light pattern is existed on the target object contained by the detection image, acquire a strip width of the structured light pattern on one region of the several regions, analyze the stripe width to determine whether the foresaid region conforms to a preset focus depth, and decide the foresaid region is compressed by a high image compression rate or a low image compression rate in accordance with a determination result of the preset focus depth.

13. The scanning apparatus of claim 9, wherein when the detection image or the decompressed image has the structured light pattern and is applied for a high image compression rate, the operation processor is adapted to further acquire line center information of specific strips of the structured light pattern, and utilize the first transceiver module to transmit the line center information; the operation module is adapted to further utilize the second transceiver module to receive the line center information for stitching of the decompressed image, and decide whether to output a switching command to the stereoscopic scanning device for decreasing the high image compression rate of the detection image in accordance with an image stitching result of the decompressed image.

14. The scanning apparatus of claim 9, wherein the stereoscopic scanning device further comprises a memory unit electrically connected with the operation processor, and adapted to store parameters about a preset ratio threshold applied for the first compression mode and a preset focus depth applied for the second compression mode.

15. A stereoscopic scanning method applied to a stereoscopic scanning device having a structured light generator and an optical sensor, the stereoscopic scanning method comprising:

driving the structured light generator to project a structured light pattern onto a target object;

driving the optical sensor to capture a detection image of the target object;

determining whether the structured light pattern is existed on the target object contained by the detection image according to analysis of the detection image;

executing a second compression mode to divide the detection image into several regions when the structured light pattern is existed on the target object contained by the detection image;

acquiring a strip width of the structured light pattern on one region of the several regions;

utilizing the stripe width to determine whether the foresaid region conforms to a preset focus depth; and deciding an image compression rate of the foresaid region in accordance with a determination result of the preset focus depth;

wherein the strip width is an average width of all stripes or partial stripes of the structured light pattern on the foresaid region.

16. The stereoscopic scanning method of claim 15, wherein the stereoscopic scanning method utilizes a low image compression rate to compress the foresaid region for transmission when the foresaid region conforms to the preset focus depth; the stereoscopic scanning method utilizes a high image compression rate to compress the foresaid region for the transmission when the foresaid region does not conform to the preset focus depth.

17. The stereoscopic scanning method of claim 15, further comprising:

setting at least one sampling line intersected with several stripes of the structured light pattern in the foresaid region; and analyzing a pixel intensity distribution curve of the at least one sampling line to acquire the strip width.

18. The stereoscopic scanning method of claim 16, further comprising:

acquiring line center information of all strips of the structured light pattern in the foresaid region when the stereoscopic scanning method utilizes the high image compression rate to compress the foresaid region; and attaching the line center information to a data packet of the compressed foresaid region for the transmission.

19. The stereoscopic scanning method of claim 18, further comprising:

acquiring a switching command relevant to an image stitching result of the compressed foresaid region and the line center information; and deciding whether to decrease the high image compression rate applied for the foresaid region in accordance with the switching command.

*   *   *   *   *